(12) United States Patent
Lindemann et al.

(10) Patent No.: US 9,433,442 B2
(45) Date of Patent: Sep. 6, 2016

(54) SPINAL CORRECTION SYSTEM AND METHOD

(71) Applicant: Warsaw Orthopedic, Inc., Warsaw, IN (US)

(72) Inventors: Gary S. Lindemann, Collierville, TN (US); Alison G. Powers, Memphis, TN (US); Keith E. Miller, Germantown, TN (US); Jeremy J. Rawlinson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 191 days.

(21) Appl. No.: 14/162,378

(22) Filed: Jan. 23, 2014

(65) Prior Publication Data

US 2015/0201973 A1 Jul. 23, 2015

(51) Int. Cl.
*A61B 17/70* (2006.01)

(52) U.S. Cl.
CPC ....... *A61B 17/7053* (2013.01); *A61B 17/7022* (2013.01)

(58) Field of Classification Search
CPC .................................................. A61B 17/7053
USPC ....... 606/246, 254, 257, 263, 272, 279, 277, 606/282, 305, 74, 105, 103
See application file for complete search history.

(56) References Cited

U.S. PATENT DOCUMENTS

| | | | | |
|---|---|---|---|---|
| 4,041,939 A * | 8/1977 | Hall | ................... | A61B 17/7022 411/304 |
| 4,697,582 A * | 10/1987 | William | ............ | A61B 17/7041 606/254 |
| 4,773,402 A * | 9/1988 | Asher | ................ | A61B 17/7002 606/250 |
| 5,092,866 A * | 3/1992 | Breard | ............... | A61B 17/7022 606/246 |
| 5,704,936 A * | 1/1998 | Mazel | ................ | A61B 17/7044 606/254 |
| 5,782,831 A * | 7/1998 | Sherman | ............ | A61B 17/7079 606/103 |
| 6,551,320 B2 * | 4/2003 | Lieberman | ......... | A61B 17/7022 606/263 |
| 2005/0043732 A1 * | 2/2005 | Dalton | ............... | A61B 17/7059 606/17 |

* cited by examiner

*Primary Examiner* — Pedro Philogene
*Assistant Examiner* — David C Comstock

(57) ABSTRACT

A spinal construct includes at least one tether extending between a first end connectable with a first fastener connected with spinal tissue and a second end connectable with a second fastener connected with spinal tissue. The at least one tether has a tension between the fasteners. A ratchet is engagable with the at least one tether to adjust the tension. Systems and methods are disclosed.

17 Claims, 11 Drawing Sheets

SPINAL CORRECTION SYSTEM AND METHOD

TECHNICAL FIELD

The present disclosure generally relates to medical devices for the treatment of musculoskeletal disorders, and more particularly to a surgical system for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment of vertebrae may employ implants, such as, for example, spinal constructs. The spinal constructs, which may include rods and bone screws, are manipulated with surgical instruments for engagement with vertebrae to position and align one or more vertebrae. This disclosure describes improvements over these prior art technologies.

SUMMARY

In one embodiment, a spinal construct is provided. The spinal construct includes at least one tether extending between a first end connectable with a first fastener connected with spinal tissue and a second end connectable with a second fastener connected with spinal tissue. The at least one tether has a tension between the fasteners. A ratchet is engagable with the at least one tether to adjust the tension.

In one embodiment, a method of treating a spine disorder is provided. The method includes the steps of: providing at least one tether extending between a first end connected to a first fastener and a second end connected to a second fastener, the at least one tether having a tension between the fasteners; providing a ratchet for connection with an intermediate portion of the at least one tether; engaging the first fastener with a first costo-vertebral surface and engaging the second fastener with a second costo-vertebral surface; and engaging the ratchet to selectively adjust the tension.

BRIEF DESCRIPTION OF THE DRAWINGS

The present disclosure will become more readily apparent from the specific description accompanied by the following drawings, in which.

DETAILED DESCRIPTION

Figure 1:
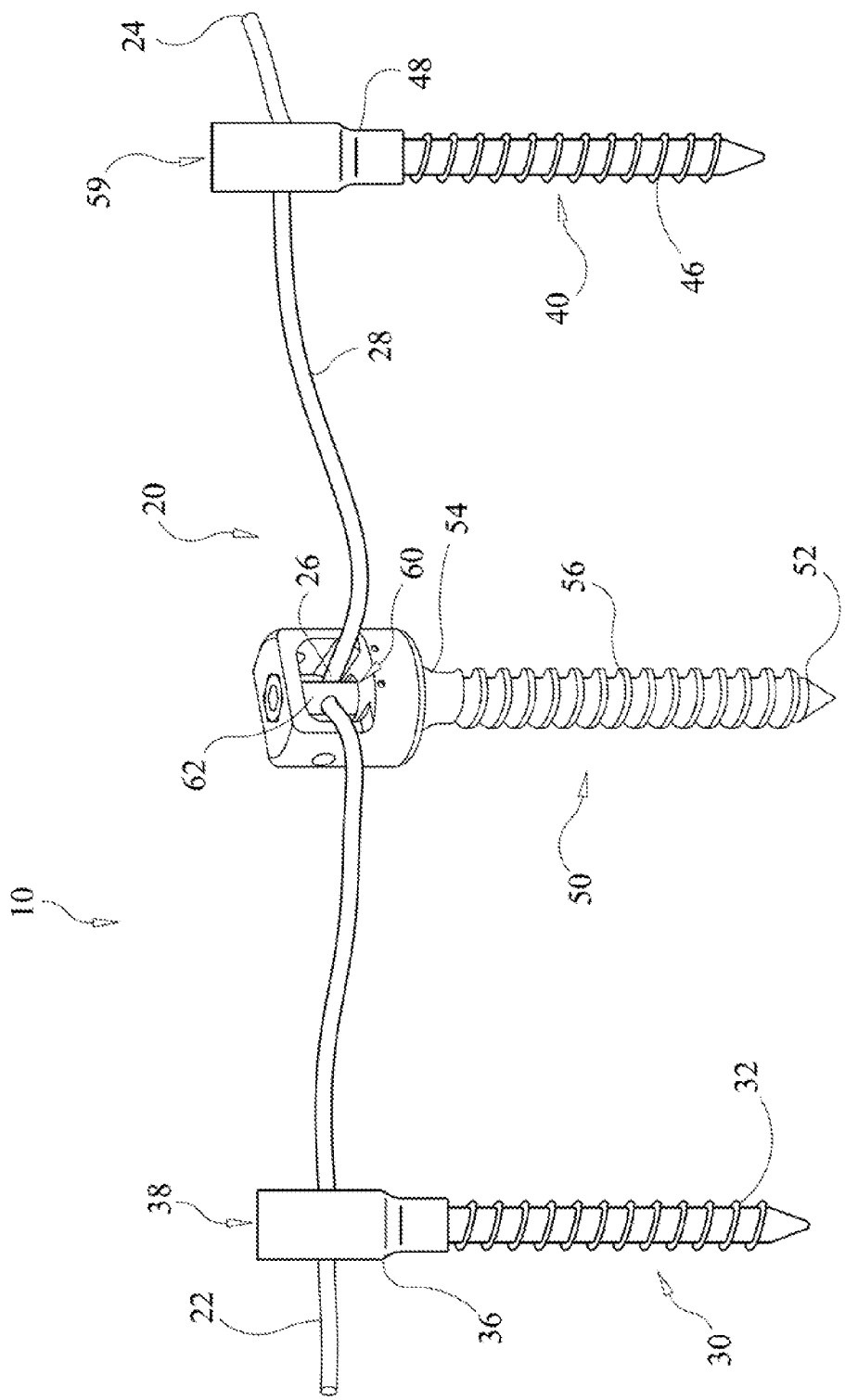
FIG. 1 is a side view of components of one embodiment of a surgical system in accordance with the principles of the present disclosure.
Figure 2:
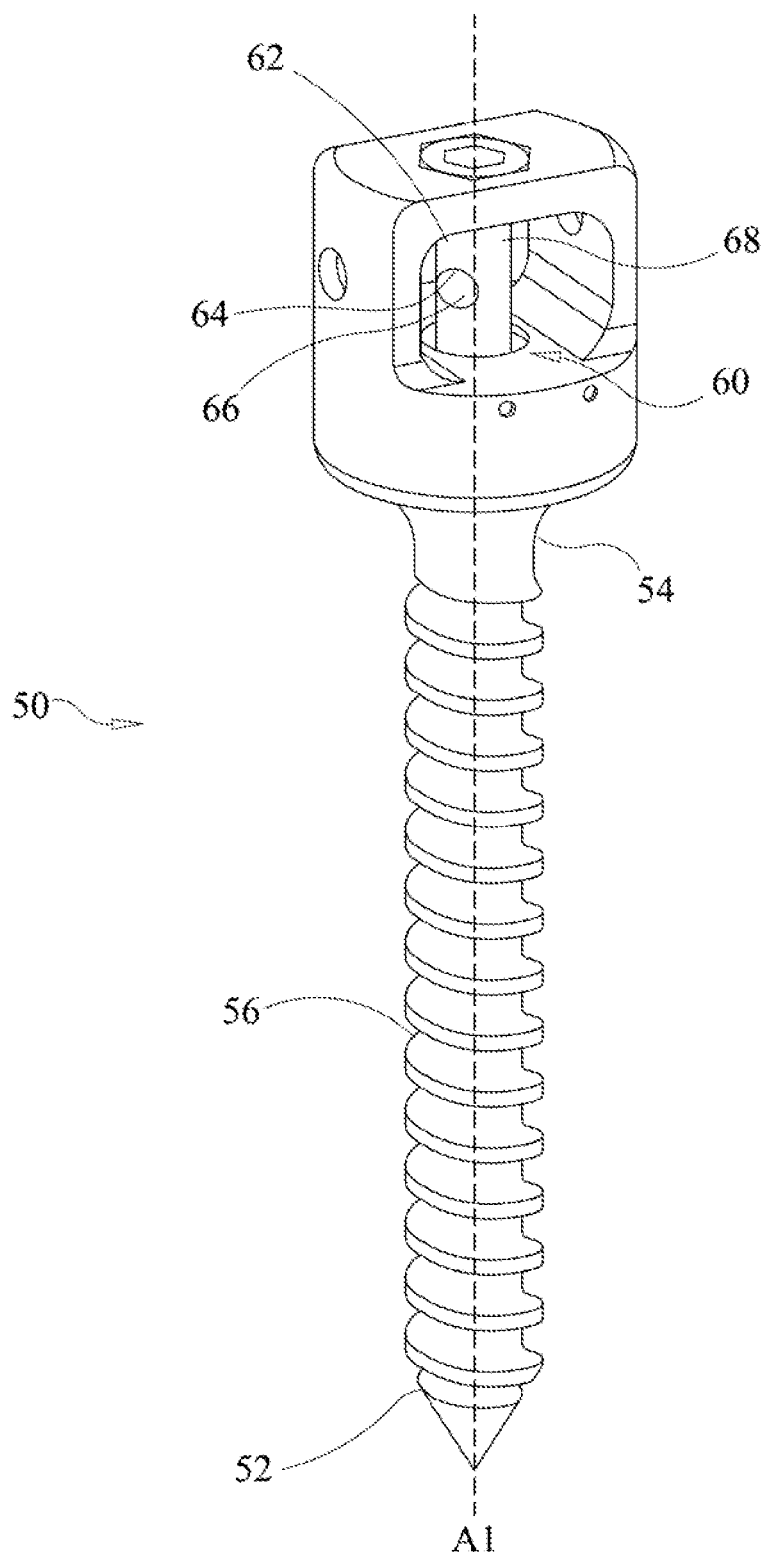
FIG. 2 is a perspective view of components shown in FIG. 1.
Figure 3:
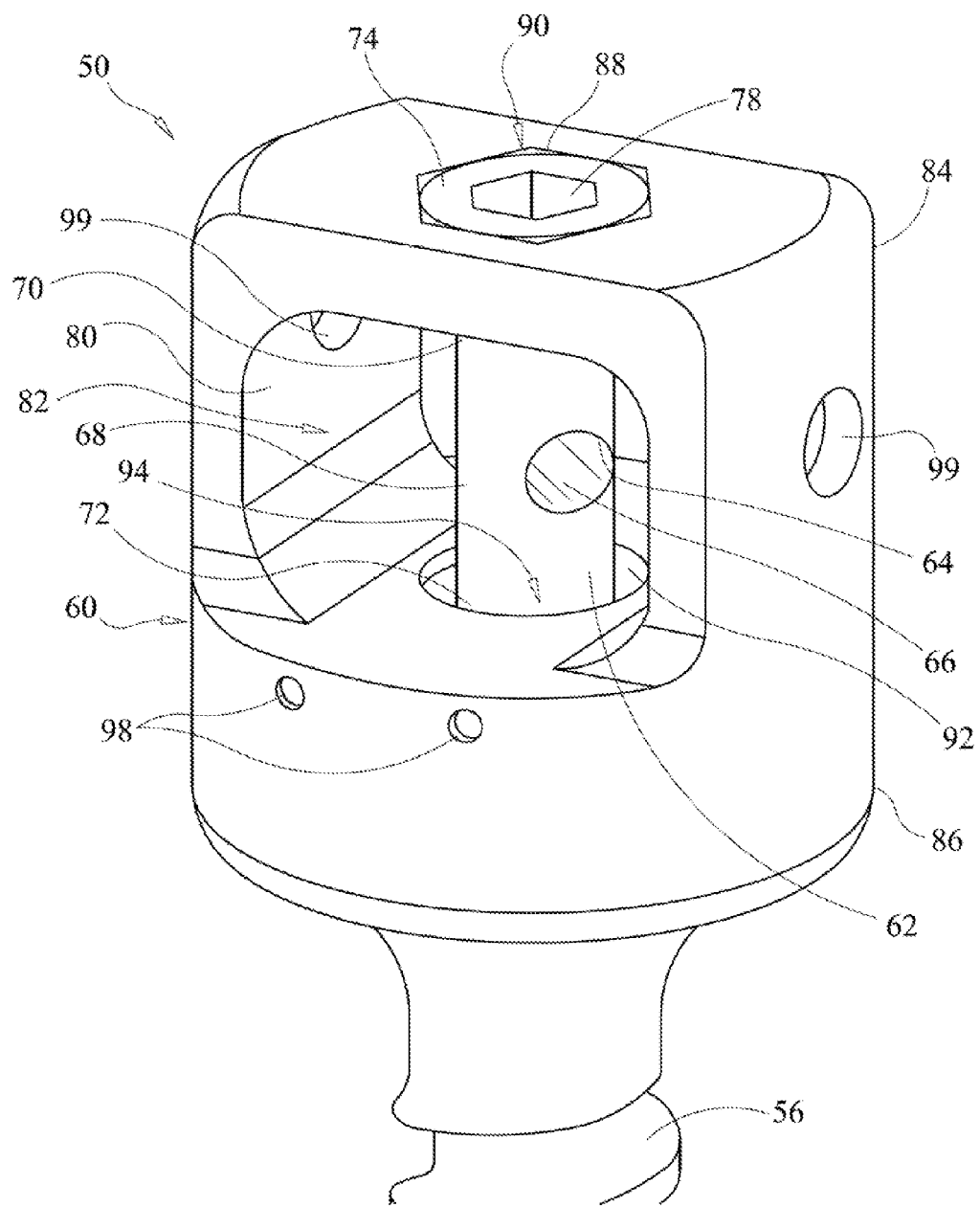
FIG. 3 is a break away view of the components shown in FIG. 2.
Figure 4:
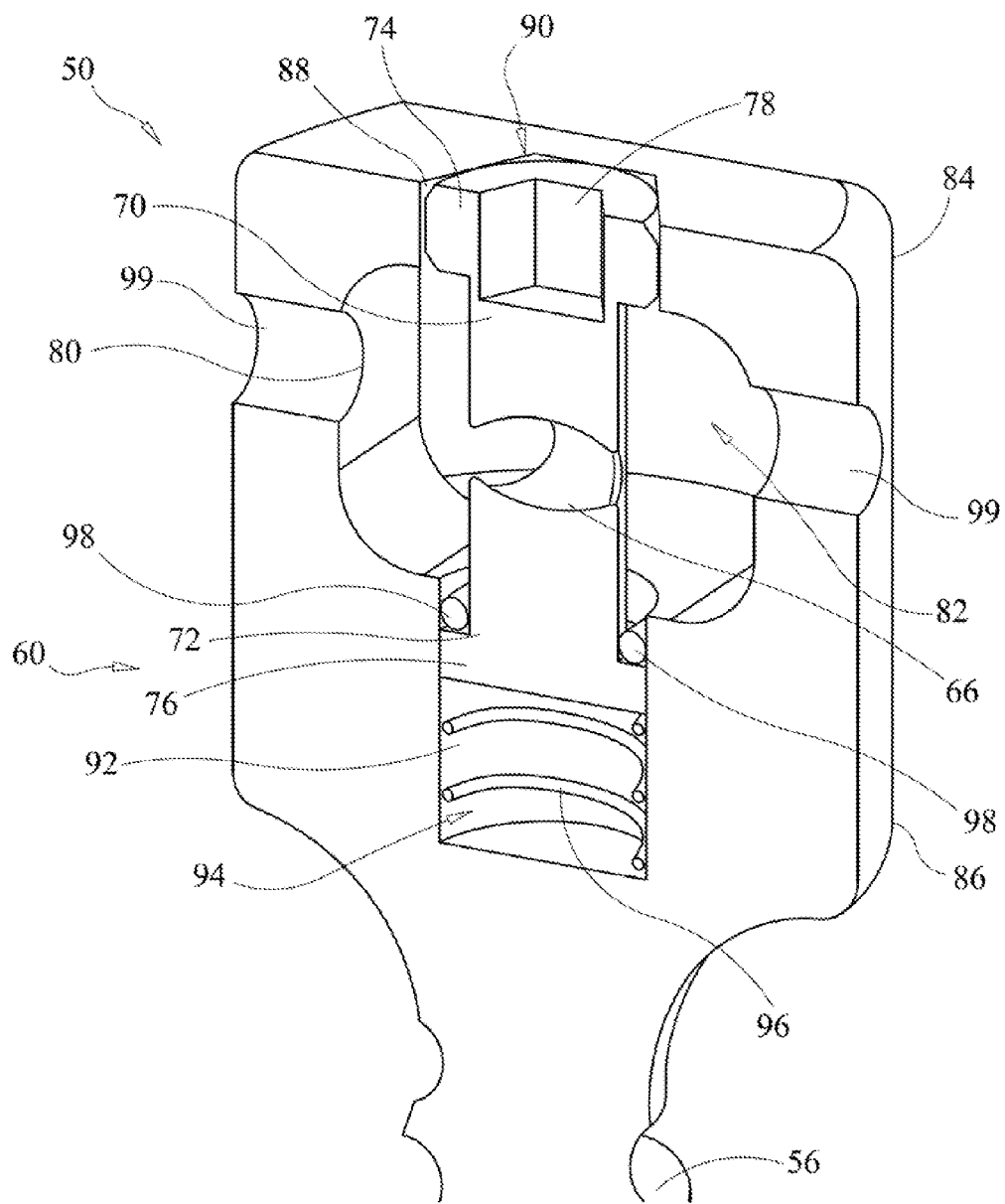
FIG. 4 is a cross section view of the components shown in FIG. 3.
Figure 5:
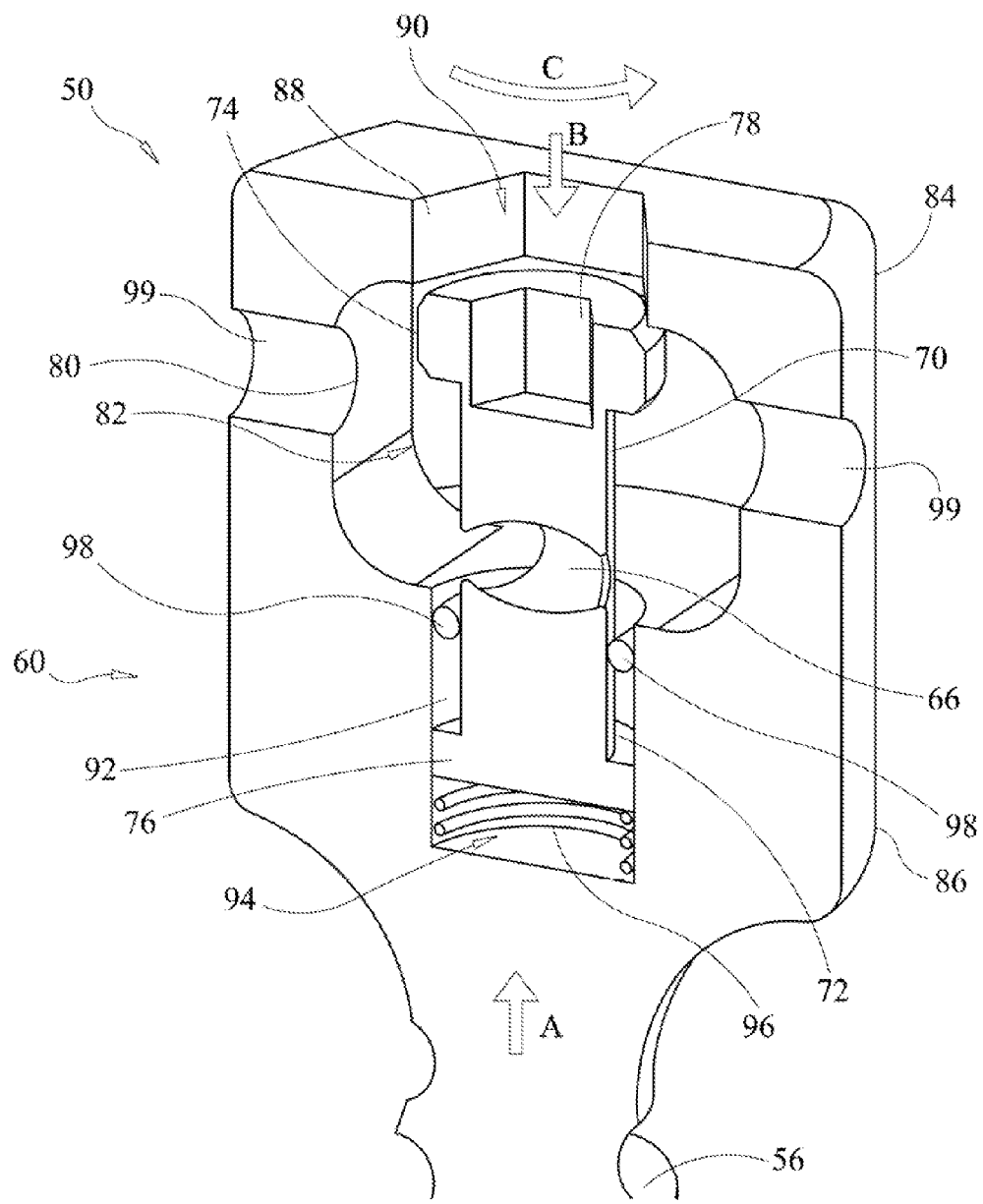
FIG. 5 is a cross section view of the components shown in FIG. 3.

The exemplary embodiments of the system and related methods of use disclosed are discussed in terms of medical devices for the treatment of musculoskeletal disorders and more particularly, in terms of a surgical system and method for correction of a spine disorder.

In one embodiment, a system includes components that can be employed with a method for deformity correction. In one embodiment, the system includes a fusionless costo-vertebral tether. In one embodiment, the system includes a tether that provides length and/or tension adjustment after the tether has been implanted at a surgical site. In one embodiment, the tether is engaged to a ratchet to adjust the tension of the tether. In one embodiment, the ratchet is engaged to or is integrally formed with a fastener, such as, for example, a bone screw. In one embodiment, the actuation, such as, for example, rotation, of the ratchet causes increase or decrease in tension of the tether. In one embodiment, the ratchet is actuated via an external magnet. In one embodiment, the ratchet is actuated percutaneously using a driver. In one embodiment, the ratchet includes a gear and a pawl configuration such that the ratchet is rotatable in a first direction to tension the tether and rotation in a second, opposite direction is resisted by the pawl. In one embodiment, the ratchet is actuated via natural movement of a patient such that when a certain threshold amount of force is experienced by the ratchet, the ratchet will rotate to a successive gear position.

In one embodiment, the ratchet includes a tether reel for adjusting the tension of the tether disposed between vertebrae. In one embodiment, the reel includes a spool engagable with the tether and rotatable relative to the reel to tension the tether. In one embodiment, the spool includes an eyelet configured for disposal of a portion of the tether, such as, for example, an intermediate portion. In one embodiment, the reel is connected to or integrally formed with a spinal fixation element, such as, for example, a spinal screw. In some embodiments, the reel is connected to or integrally formed with various components, such as, for example, a spinal hook or other spinal fixation devices. In one embodiment, the tether reel is not connected to or integrally formed with a bone fixation element. In one embodiment, the tether reel is engaged to the tether between bone fixation points and tension of the tether between the bone fixation points is adjusted by rotating the tether reel. In one embodiment, a bone fastener including the reel is engaged to spinal tissue in various orientations, such as, for example, anterior or anterior laterally in a vertebral body, posteriorly in vertebral pedicles, vertebral facets, a head of a rib and/or adjacent a costo-vertebral space.

In one embodiment, the system includes a reel having a spool drive configured for mating engagement with a driver for driving the rotation of the reel. In one embodiment, the reel includes an opening for an inserter attachment. In one embodiment, the reel includes a spool lock configured to resist and/or prevent the spool from turning relative to the reel. In one embodiment, the reel includes cross pins configured to keep the spool assembled to the reel. In one embodiment, the reel includes a biasing member, such as, for example, a spring to resiliently bias the spool to a position such that the spool is engaged with the spool lock. In operation, the driver is positioned within the spool drive and a downward force is applied to the driver to overcome the resilient bias of the spring and disengage the spool from the spool lock. With the spool disengaged from the spool lock, the spool is rotated to wind the tether about the spool to tension the tether. The driver is disengaged from the spool drive such that the spool is biased into engagement with the spool lock resisting and/or preventing the tether from unwinding. In one embodiment, a method of operating the tether reel is provided. The method includes positioning a bone fastener, such as, for example, a bone screw into bony anatomy, threading the tether through the eyelet of the spool, and applying tension to the tether by rotating the spool.

In one embodiment, the system includes a tether placed on an anterior column of a spine to correct scoliosis and/or a convex side of a scoliotic curve. As the spine grows, the tether pulls the curve into a more linear orientation. In one embodiment, the system includes tethers placed on a posterior side of a spine in a space, such as, for example, a costo-vertebral space between a superior costal facet and a transverse costal facet, which is between the transverse process and a rib. In one embodiment, the system includes clamps attached to the tether and a costo-vertebral surface. In one embodiment, the system includes clamps having a diameter that is larger than the costo-vertebral space. Tension between each clamp applies correction forces to the spine. In one embodiment, the clamp has a C-shaped configuration defining a cavity and a lock screw to capture an end of the tether in the cavity. In one embodiment, the C-shaped clamp includes a compression plate disposed between the tether and the lock screw. In one embodiment, the clamp includes a first portion and a second portion movable relative to the first portion. The first and second portions define a cavity therebetween configured for disposal of the tether. A lock screw moves the first and second portions of the clamp relative to one another to capture the tether within the cavity. In one embodiment, the first portion defines at least one notch and the second portion defines at least one rib in coaxial alignment with the at least one notch to capture the tether within the cavity between the first and second portions. In one embodiment, the at least one rib enhances grip strength on the tether.

In one embodiment, the system includes a tether reel positioned along the tether to adjust tension between fixation points. In one embodiment, the reel is directly connected to a fixation point, such as, for example, a screw or a staple. In one embodiment, the reel is connected to the tether between fixation points. In one embodiment, tension is adjusted during implantation surgery. In one embodiment, tension is adjusted post-op via small incisions. In one embodiment, a first tether is engaged to a first fixation point and the tether reel and a second tether is engaged to a second fixation point including the tether reel and a third fixation point such that a tension of the first tether is adjustable and a tension of the second tether is fixed. In one embodiment, the reel is a free floating reel engaged with the tether between two fixation points.

In some embodiments, one or all of the components of a spinal correction system may be disposable, peel-pack, pre-packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or 'approximately' another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

The following discussion includes a description of a system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a system, such as, for example, a spinal correction system 10 in accordance with the principles of the present disclosure.

The components of system 10 can be fabricated from biologically acceptable materials suitable for medical applications, including metals, synthetic polymers, ceramics, bone material, tissue and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a longitudinal element, such as, for example, a tether 20 extending between an end 22 and an end 24. Tether 20 has a tension or tensile force measured between ends 22, 24. In some embodiments, the tension of tether 20 between ends 22, 24 is defined as a tensile force, for example measured in Newtons (N) or pounds, which is a pulling force exerted by tether 20 on ends 22, 24 to draw tether 20 taught and apply the tension in the direction of tether 20 to selected vertebrae for treating a spine, as described herein. Ends 22, 24 are connected to the selected vertebrae via fasteners, as described herein, such that the selected vertebrae and the spine experience a pulling force equal to the tension.

Tether 20 includes an intermediate portion 26 disposed between ends 22, 24. Tether 20 has a flexible configuration, which includes movement in a lateral or side to side direction and prevents expanding and/or extension in an axial direction upon fixation with vertebrae, as described herein. In some embodiments, all or only a portion of tether 20 may have a semi-rigid, rigid or elastic configuration, and/or have elastic properties such that tether 20 provides a selective amount of expansion and/or extension in an axial direction. In some embodiments, tether 20 may be compressible in an axial direction. Tether 20 can include a plurality of separately attachable or connectable portions or sections, such as bands or loops, or may be monolithically formed as a single continuous element.

Tether 20 has an outer surface 28 and a uniform thickness/diameter. In some embodiments, outer surface 28 may have various surface configurations, such as, for example, rough, threaded for connection with surgical instruments, arcuate, undulating, porous, semi-porous, dimpled, polished and/or textured according to the requirements of a particular application. In some embodiments, the thickness defined by tether 20 may be uniformly increasing or decreasing, or have alternate diameter dimensions along its length. In some embodiments, tether 20 may have various cross section configurations, such as, for example, oval, oblong, triangular, rectangular, square, polygonal, irregular, uniform, non-uniform, variable and/or tapered.

In some embodiments, tether 20 may have various lengths. In some embodiments, tether 20 may be braided, such as a rope, or include a plurality elongated elements to provide a predetermined force resistance. In some embodiments, tether 20 may be made from autograft and/or allograft, as described herein, and be configured for resorbable or degradable applications.

In some embodiments, the longitudinal element may include one or a plurality of flexible wires, staples, cables, ribbons, artificial and/or synthetic strands, rods, plates, springs, and combinations thereof. In one embodiment, the longitudinal element is a cadaver tendon. In one embodiment, the longitudinal element is a solid core. In one embodiment, the longitudinal element is tubular.

System 10 includes a fastener, such as, for example, a bone screw 30 connected with spinal tissue and connectable with end 22 of tether 20. System 10 includes a fastener, such as, for example, a bone screw 40 connected with spinal tissue and connectable with end 24 of tether 20. Tether 20 has a tension between bone screws 30, 40, as described herein. Bone screws 30, 40 may be monolithically formed, integrally connected or attached with fastening elements to tether 20. In some embodiments, one or a plurality of bone screws may be connected with tether 20.

Bone screws 30, 40, are configured for penetrating fixation with tissue of vertebrae along a plurality of vertebral levels. Each of bone screws 30, 40, is disposed to engage a separate vertebral level. In some embodiments, one or a plurality of fasteners may be employed with a single vertebral level. In some embodiments, bone screws 30, 40 may be engaged with vertebrae in various orientations, such as, for example, series, parallel, offset, staggered and/or alternate vertebral levels. In some embodiments, the fasteners may include one or a plurality of anchors, tissue penetrating screws, conventional screws, expanding screws, wedges, anchors, buttons, hooks, clips, snaps, friction fittings, compressive fittings, expanding rivets, staples, nails, adhesives, posts, fixation plates and/or posts. These fasteners may be coated with an osteoinductive or osteoconductive material to enhance fixation, and/or include one or a plurality of therapeutic agents.

In some embodiments, system 10 includes a fastener, such as, for example, a bone screw 50 configured for penetrating tissue, such as, for example, spinal tissue between bone screw 30 and bone screw 40. Bone screw 50 extends between an end 52 and an end 54 defining a longitudinal axis A1 therebetween. End 52 includes a threaded shaft 56 configured for penetrating engagement with spinal tissue. End 54 includes a ratchet 60 engagable with a portion of tether 20, such as, for example, intermediate portion 26 to adjust the tension of tether 20, as described herein. In some embodiments, ratchet 60 is configured to dynamically adjust the tension of tether 20. In some embodiments, ratchet 60 is configured to adjust tether 20 to a selected tension. In one embodiment, ratchet 60 is configured for magnetic actuation to adjust the tension of tether 20.

Ratchet 60 includes a rotatable reel, such as, for example, a spool 62 engagable with tether 20 to selectively adjust the tension of tether 20. Spool 62 is lockable to prevent rotation thereof. Spool 62 is movable between a first configuration, such as, for example, a non-locked configuration, such that spool 62 is rotatable relative to ratchet 60 and a second configuration, such as, for example, a locked configuration, such that the rotation of spool 62 is resisted and/or prevented, as described herein. Spool 62 includes an inner surface 64 defining a bore, such as, for example an eyelet 66, configured for disposal of tether 20. Rotation of spool 62 relative to ratchet 60 disposes tether 20 about spool 62 such that tether 20 encircles and is wound about spool 62. Such rotation of spool 62 adjusts the tension of tether 20 between ends 22, 24. Spool 62 includes a cylindrical configuration and an outer surface 68. Spool 62 is disposed in coaxial alignment with axis A2. In some embodiments, spool 62 is variously shaped and configured, such as, for example, oval, oblong, rectangular, triangular, square, polygonal, irregular, uniform, non-uniform, offset, staggered, undulating, arcuate, variable and/or tapered. In some embodiments, outer surface 68 may include one or a plurality of openings. In some embodiments, all or only a portion of outer surface 68 may have alternate surface configurations, such as, for example, smooth, rough, arcuate, undulating, mesh, porous, semi-porous, dimpled and/or textured. In some embodiments, all or only a portion of spool 62 may be disposed at alternate orientations, relative to axis A1 of bone screw 50, such as, for example, transverse, perpendicular and/or other angular orientations such as acute or obtuse, co-axial and/or may be offset or staggered. In some embodiments, all or only a portion of spool 62 may be cannulated.

Spool 62 extends between an end 70 and an end 72. End 70 includes a male mating part 74 projecting radially from outer surface 68 and configured for engagement with an opening 90 of ratchet 60 in the locked configuration, as described herein. End 72 includes a radial extension, such as, for example, a circumferential ledge 76, projecting radially from outer surface 68. Male mating part 74 and ledge 76 each include an arcuate configuration. In some embodiments, male mating part 74 and ledge 76 are variously configured, such as, for example, those alternatives described herein. End 70 defines a hexagonal socket 78 configured for mating engagement with a driving tool (not shown) to rotate spool 62 relative to ratchet 60 to adjust the tension of tether 20. In some embodiments, socket 78 may be variously configured, such as, for example, Phillips head, slotted head, hex socket head, hexagon external head, frearson head, square socket, square slotted combination head, spanner drilled tamper proof head and combinations thereof.

Ratchet 60 includes an inner surface 80 defining a cavity 82 having spool 62 disposed therein. Cavity 82 extends through a thickness of ratchet 60 to provide access to spool 62 and space about spool 62 for tether 20 as tether 20 is inserted into cavity 82 and winds about spool 62 during selective tensioning of tether 20. Ratchet 60 extends between an end 84 and an end 86. End 84 includes an inner surface 88 defining a cavity, such as, for example, opening 90 extending proximally from cavity 82. Opening 90 has a hexagonal configuration and is configured for disposal of male mating part 74 of spool 62 in the locked configuration. With spool 62 in the locked configuration, male mating part 74 of spool 62 and inner surface 88 of end 84 are engaged in an interference fit such that inner surface 88 resists the relative rotation of spool 62. In some embodiments, opening 90 is variously configured, such as, for example, those alternatives described herein.

End 86 includes an inner surface 92 defining a cavity, such as, for example, a passageway 94, configured for disposal of end 72 of spool 62. Passageway 94 extends distally from cavity 82 such that passageway 94, cavity 82, and opening 90 are continuous, with spool 62 being axially translatable therethrough. Ratchet 60 includes a biasing member, such as, for example, a spring 96, disposed in passageway 94 between end 86 of ratchet 60 and end 72 of spool 62 to resiliently bias spool 62 to the locked configuration. Ratchet 60 includes a capture member, such as, for example, a pair of elongate members 98 extending into passageway 94 configured to maintain ledge 76 of spool 62 in passageway 94. Elongate members 98 are disposed in a parallel orientation relative to one another and are spaced apart a distance substantially equal to a diameter of spool 62. Spring 96 resiliently biases spool 62, in a direction shown by arrow A in FIG. 5, to dispose ledge 76 of spool 62 with elongate members 98 such that elongate members 98 resist and/or prevent further movement of spool 62. Ratchet 60 includes a cavity 99 configured for attachment to a surgical instrument (not shown), such as, for example, an extender or inserter for inserting bone screw 50 into spinal tissue. In some embodiments, cavity 99 comprises a recess defined with the outer surface of ratchet 60 and does not extend completely through the wall of ratchet 60.

In operation, tether 20 is inserted into cavity 82 and is disposed into eyelet 66. The driving tool (not shown) is engaged with socket 78 and a force is applied to spool 62, in a direction shown by arrow B in FIG. 5, to overcome the resilient bias of spring 96. Spool 62 axially translates from the locked configuration to the non-locked configuration such that male mating part 74 of spool 62 and inner surface 88 of ratchet 60 are disengaged. With spool 62 in the non-locked configuration, spool 62 is rotated, in a direction shown by arrow C in FIG. 5, disposing tether 20 about spool 62 tensioning tether 20 between bone screw 30 and bone screw 40. Rotating spool 62 in a direction opposite the direction shown by arrow C unwinds tether 20 to reduce tension in tether 20.

In assembly, operation and use, spinal correction system 10, similar to the systems described herein, is employed with a surgical procedure, such as, for a correction treatment to treat adolescent idiopathic scoliosis and/or Scheuermann's kyphosis of a spine. In some embodiments, one or all of the components of spinal correction system 10 can be delivered or implanted as a pre-assembled device or can be assembled in situ. Spinal correction system 10 may be completely or partially revised, removed or replaced. In some embodiments, spinal correction system 10 includes fusionless treatment of vertebrae.

Figure 6:
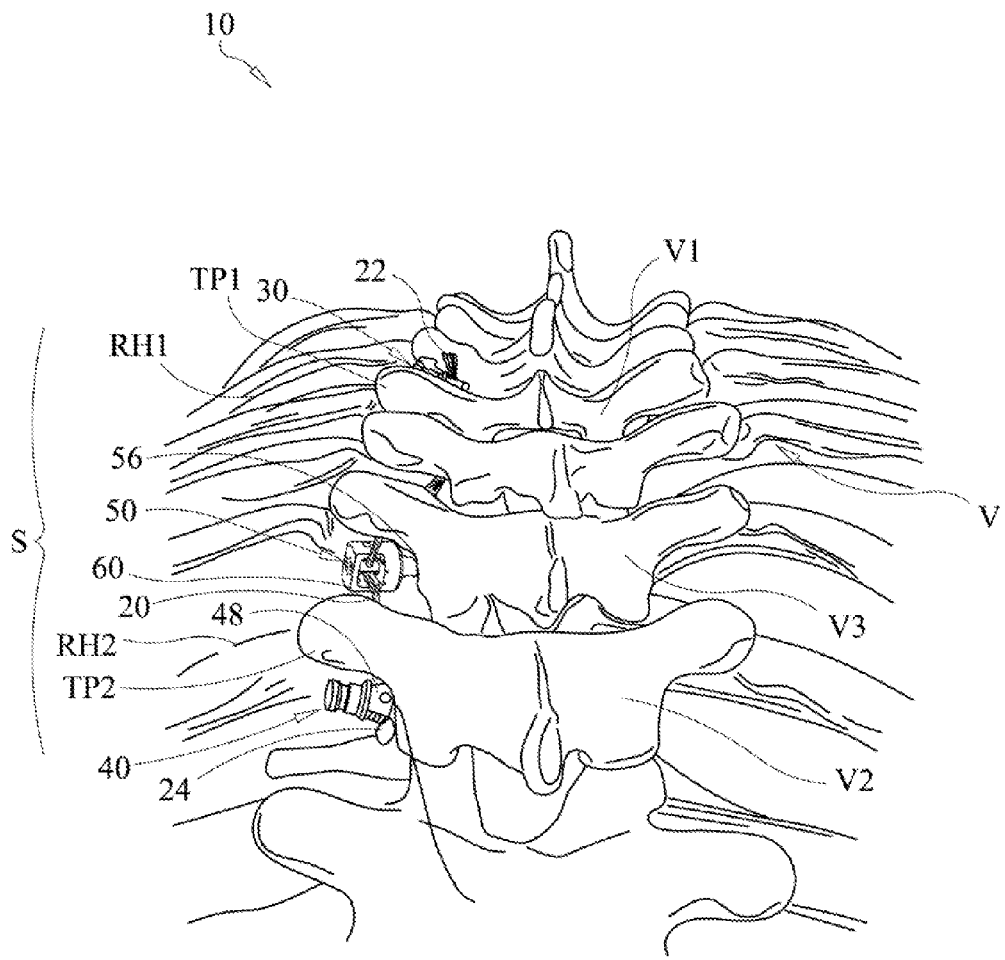
FIG. 6 is a perspective view of components of one embodiment of a surgical system in accordance with the principles of the present disclosure disposed with vertebrae.

For example, as shown in FIG. 6, spinal correction system 10 can be employed with a surgical correction treatment of an applicable condition or injury of an affected section of a spinal column and adjacent areas within a body, such as, for example, a vertebra V1, a vertebra V2 and a plurality of vertebra V3 disposed therebetween.

In use, to treat a selected section S of vertebrae V, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder. The configuration and dimension of tether 20 is determined according to the configuration and dimension of selected section S.

An incision is made in the body of a patient and a cutting instrument (not shown) creates a surgical pathway along a substantially posterior approach for implantation of components of spinal correction system 10 within the patient body. A sleeve or cannula is used to access a costo-vertebral space adjacent vertebra V1 and facilitate delivery and access for components of spinal correction system 10 along the surgical pathway, for example, such that tether 20 is disposed in a costo-vertebral space between costo-vertebral surfaces, which include surfaces of a transverse process TP1, a rib head RH1 and vertebra V1. In some embodiments, this method and configuration avoid undesired engagement with body structures, such as, for example, a spinal canal and vascular structures, in that the surgical pathway is created via muscle-splitting through relatively bloodless planes. A preparation instrument (not shown) can be employed to prepare tissue surfaces of vertebrae V and adjacent rib surfaces, as well as for aspiration and irrigation of the region.

Bone screw 30 is configured to support a tensile load with tether 20 over costo-vertebral surfaces, which include surfaces of transverse process TP1 and rib head RH1. A pilot hole is made in vertebra V1 for receiving bone screw 30. Bone screw 30 is delivered along the surgical pathway adjacent the costo-vertebral space for penetrating engagement with vertebra V1. Bone screw 30 includes a threaded bone engaging portion 32 that is inserted or otherwise engaged with vertebra V1. Bone screw 30 has a head 36 with a bore, or through opening and a set screw 38, which is torqued on to tether 20 such that end 22 of tether is connected with bone screw 30.

A pilot hale is made in vertebra V3 for receiving bone screw 50. Bone screw 50 is delivered along the surgical pathway, or an alternate surgical pathway along a substantially posterior approach, adjacent a costo-vertebral space for penetrating engagement with vertebra V3. Shaft 56 bone screw 50 is inserted or otherwise engaged with vertebra V3.

Bone screw 40 is configured to support a tensile bad with tether 20 over costo-vertebral surfaces, which include surfaces of a transverse process TP2, a rib head RH2 and vertebra V2. A pilot hole is made in vertebra V2 for receiving bone screw 40. Bone screw 40 is delivered along the surgical pathway, or an alternate surgical pathway along a substantially posterior approach, adjacent a costo-vertebral space for penetrating engagement with vertebra V2. Bone screw 40 includes a threaded bone engaging portion 46 that is inserted or otherwise engaged with vertebra V2. Bone screw 40 has a head 48 with a bore, or through opening and a set screw 59, which is torqued on to tether 20.

Tether 20 is delivered along the surgical pathway to the costo-vertebral space for attachment with bone screw 30. Set screw 38 of head 36 is torqued on to the portion of tether 20 disposed with bone screw 30 to securely fix end 22 of tether 20 with vertebra V1. Tether 20 is disposed in the costo-vertebral space on a posterior side of vertebra V1 such that tether 20 is disposed on an anterior side of transverse process TP1.

Tether 20 is threaded in a costo-transverse orientation along vertebra V1 and one or a plurality of vertebra V3 to dispose intermediate portion 26 of tether 20 in eyelet 66 of spool 62. Tether 20 is disposed in the costo-vertebral space on a posterior side of vertebra V3 such that tether 20 is disposed on an anterior side of transverse process TP3.

Tether 20 is threaded in a costo-transverse orientation along vertebra V3 and vertebra V2. Set screw 59 of head 48 is torqued on to the portion of tether 20 disposed with bone screw 40 to securely fix end 24 of tether 20 with vertebra V2. Tether 20 is disposed in the costo-vertebral space on a posterior side of vertebra V2 such that tether 20 is disposed on an anterior side of transverse process TP2.

The driving tool (not shown) is engaged with socket 78 and a force is applied to spool 62, in a direction shown by arrow B, to overcome the resilient bias of spring 96. Spool 62 axially translates from the locked configuration to the non-locked configuration such that male mating part 74 of spool 62 and inner surface 88 of ratchet 60 are disengaged. With spool 62 in the non-locked configuration, spool 62 is rotated, in a direction shown by arrow C, encircling and winding tether 20 about spool 62 to increase tension of tether 20 between bone screw 30 and bone screw 40. Tether 20 exerts a tensile pulling force on ends 22, 24 to draw tether 20 taught and apply the tension in the direction of tether 20 to vertebrae V for treating the spine. Vertebrae V and the spine experience a pulling force equal to the tension. Rotating spool 62 in a direction opposite the direction shown by arrow C unwinds tether 20 to reduce tension in tether 20.

The components of spinal correction system 10 are attached with a first side, such as, for example, a convex side of vertebrae V to prevent growth of selected section S, while allowing for growth and adjustments to a second side, such as, for example, a concave side of vertebrae V to provide treatment. Compression of section S of vertebrae V occurs along convex side. In some embodiments, spinal correction system 10 implants components along a sagittal plane of a patient such that tether 20 is disposed anterior to a pedicle to reduce undesired lordosis. In some embodiments, spinal correction system 10 implants components along a coronal plane of a patient whereby tether 20 is disposed in a lateral orientation relative to a pedicle to provide correction in the coronal plane.

In one embodiment, spinal correction system 10 includes an agent, which may be disposed, packed, coated or layered within, on or about the components and/or surfaces of spinal correction system 10. In some embodiments, the agent may include bone growth promoting material, such as for example, bone graft to enhance fixation of the fixation elements with vertebrae V.

Upon completion of the procedure, the surgical instruments, assemblies and non-implanted components of spinal correction system 10 are removed and the incision is closed. Spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

Figure 7:
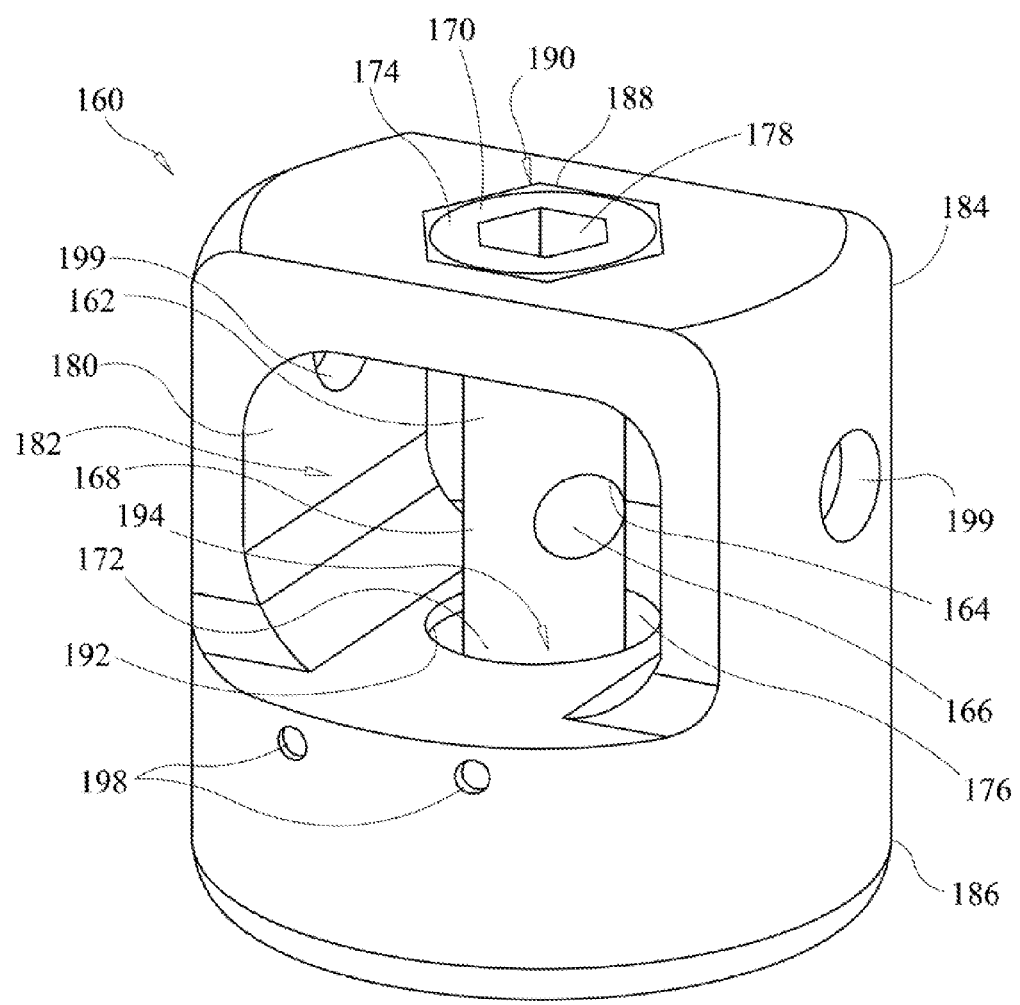
FIG. 7 is a perspective view of components of one embodiment of a surgical system in accordance with the principles of the present disclosure.

In one embodiment, as shown in FIG. 7, system 10, similar to the systems and methods described with regard to FIGS. 1-6, includes a ratchet 160, similar to ratchet 60 as described herein. Ratchet 160 is free floating between bone screws 30, 40 and in engagement with intermediate portion 26 of tether 20 to tension tether 20 therebetween. Ratchet 160 includes a rotatable reel, such as, for example, a spool 162, similar to spool 62 described herein. Spool 162 is engageable with tether 20 to selectively adjust the tension of tether 20. Spool 162 is lockable to prevent rotation thereof. Spool 162 is movable between a first configuration, such as, for example, a non-locked configuration, such that spool 162 is rotatable relative to ratchet 160 and a second configuration, such as, for example, a locked configuration, such that the rotation of spool 162 is resisted and/or prevented, as described herein. Spool 162 includes an inner surface 164 defining a bore, such as, for example an eyelet 166, configured for disposal of tether 20. Rotation of spool 162 relative to ratchet 160 disposes or winds tether 20 thereabout to adjust the tension of tether 20 between ends 22, 24 thereof.

Spool 162 extends between an end 170 and an end 172. End 170 includes a male mating part 174 projecting radially from an outer surface 168 of spool 162. Male mating part 174 is configured for engagement with an opening 190 of ratchet 160 in the locked configuration, as described herein. End 172 includes a radial extension, such as, for example, a circumferential ledge 176, projecting radially from outer surface 168. End 170 defines a hexagonal socket 178 configured for mating engagement with a driving tool (not shown) to rotate spool 162 relative to ratchet 160 to adjust the tension of tether 20.

Ratchet 160 includes an inner surface 180 defining a cavity 182 having spool 162 disposed therein. Ratchet 160 extends between an end 184 and an end 186. End 184 includes an inner surface 188 defining a cavity, such as, for example, opening 190 extending proximally from cavity 182. Opening 190 has a hexagonal configuration and is configured for disposal of male mating part 174 of spool 162 in the locked configuration. With spool 162 in the locked configuration, male mating part 174 of spool 162 and inner surface 188 of end 184 are engaged in an interference fit such that inner surface 188 resists the relative rotation of spool 162.

End 186 includes an inner surface 192 defining a cavity, such as, for example, a passageway 194, configured for disposal of end 172 of spool 162. Passageway 194 extends distally from cavity 182 such that passageway 194, cavity 182, and opening 190 are continuous, with spool 162 being axially translatable therethrough. Spool 162 is resiliently biased to the locked configuration. Ratchet 160 includes a capture member, such as, for example, a pair of elongate members 198 extending into passageway 194 configured to maintain ledge 176 of spool 162 in passageway 194. Elongate members 198 are disposed in a parallel orientation relative to one another and are spaced apart a distance substantially equal to a diameter of spool 162. Ratchet 160 includes a cavity 199, similar to cavity 99 described herein, configured for attachment to a surgical instrument (not shown) for inserting bone screw 50 into spinal tissue.

Figure 8:
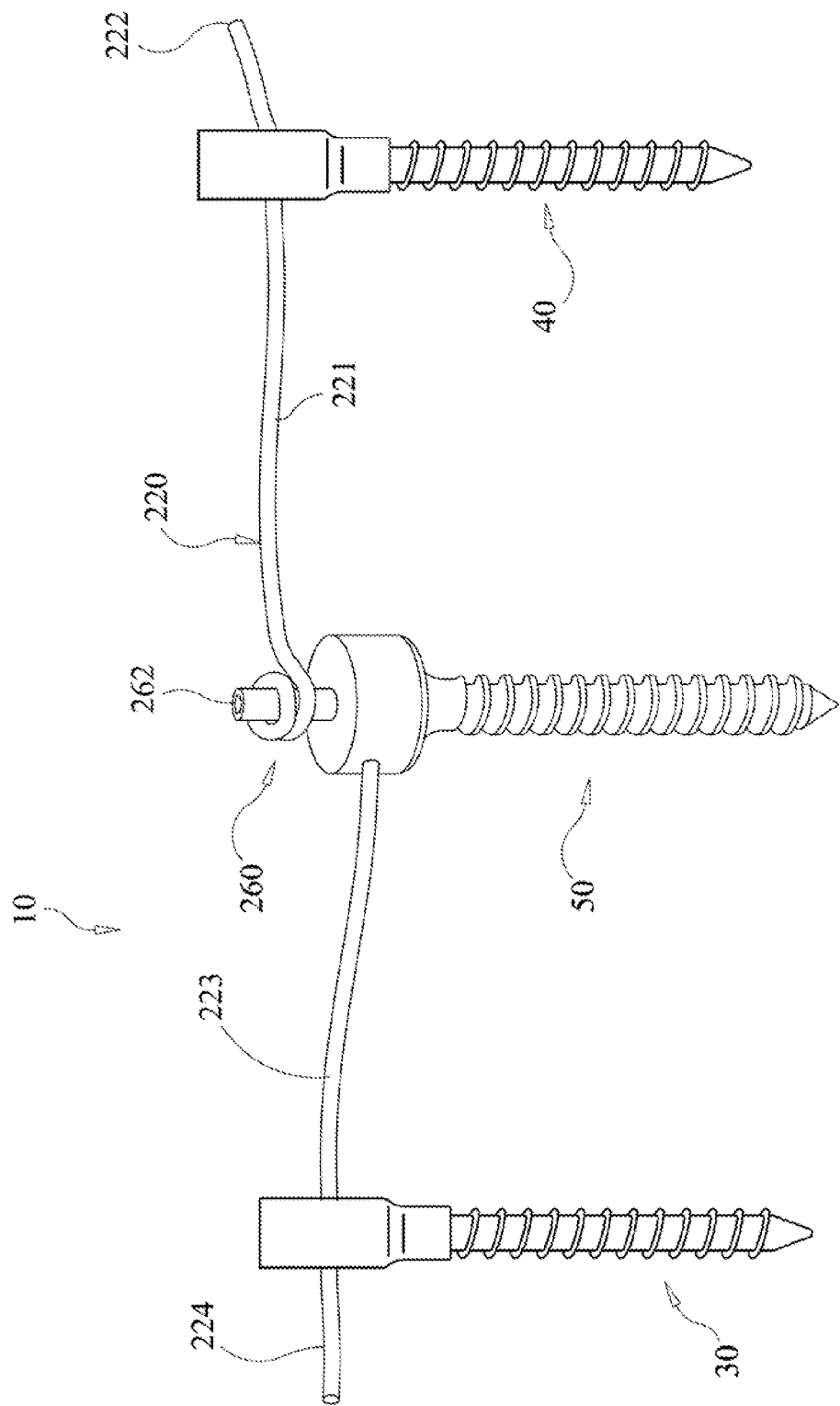
FIG. 8 is a perspective view of components of one embodiment of a surgical system in accordance with the principles of the present disclosure.

In one embodiment, as shown in FIG. 8, system 10, similar to the systems and methods described with regard to FIGS. 1-6, includes a longitudinal element, such as, for example, a tether 220, similar to tether 20 described herein, extending between an end 222 and an end 224. Tether 220 includes a tether 221 and a tether 223. Tether 221, which includes end 222 of tether 220 has an adjustable tension and is connected with bone screw 40 and a ratchet 260 of bone screw 50, similar to ratchet 60 described herein, such that the actuation of ratchet 260 adjusts the tension of tether 221 between bone screw 40 and bone screw 50. Tether 223, which includes end 224 of tether 220 has a fixed tension and is connected with bone screw 30 and bone screw 50 such that the actuation of ratchet 260 does not adjust the tension of tether 223. Ratchet 260 includes a rotatable reel, such as, for example, a spool 262, similar to spool 62 described herein. Spool 262 is movable between a first configuration such that spool 262 is rotatable to wind tether 221 thereabout and a second configuration such that rotation of spool 262 is resisted and/or prevented to fix the tension of tether 220.

Figure 9:
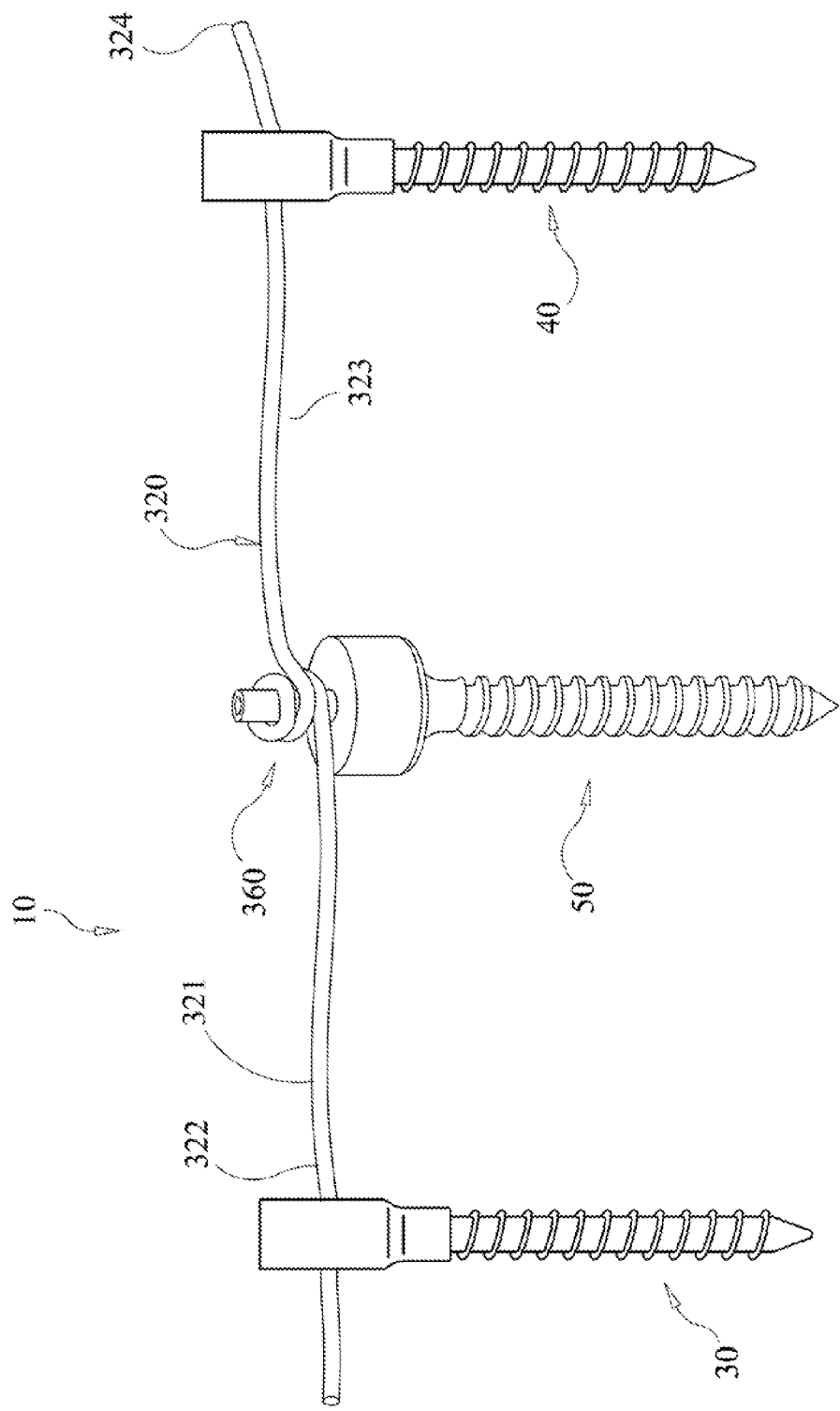
FIG. 9 is a perspective view of components of one embodiment of a surgical system in accordance with the principles of the present disclosure.

In one embodiment, as shown in FIG. 9, system 10, similar to the systems and methods described herein, includes a longitudinal element, such as, for example, at least one tether 320, similar to tether 20 described herein, extending between an end 322 and an end 324. Tether 320 includes a tether 321 and a tether 323. Tether 321 which includes end 322 of tether 320 has an adjustable tension and is connected to bone screw 30 and a ratchet 360 of bone screw 50, similar to ratchet 260 described with regard to FIG. 8. Tether 323, which includes end 324 of tether 320 has an adjustable tension and is connected to bone screw 40 and ratchet 360. The actuation of ratchet 360 winds tethers 321, 323 about ratchet 360 to tension tether 320 between ends 322, 324 of tether 320.

Figure 10:
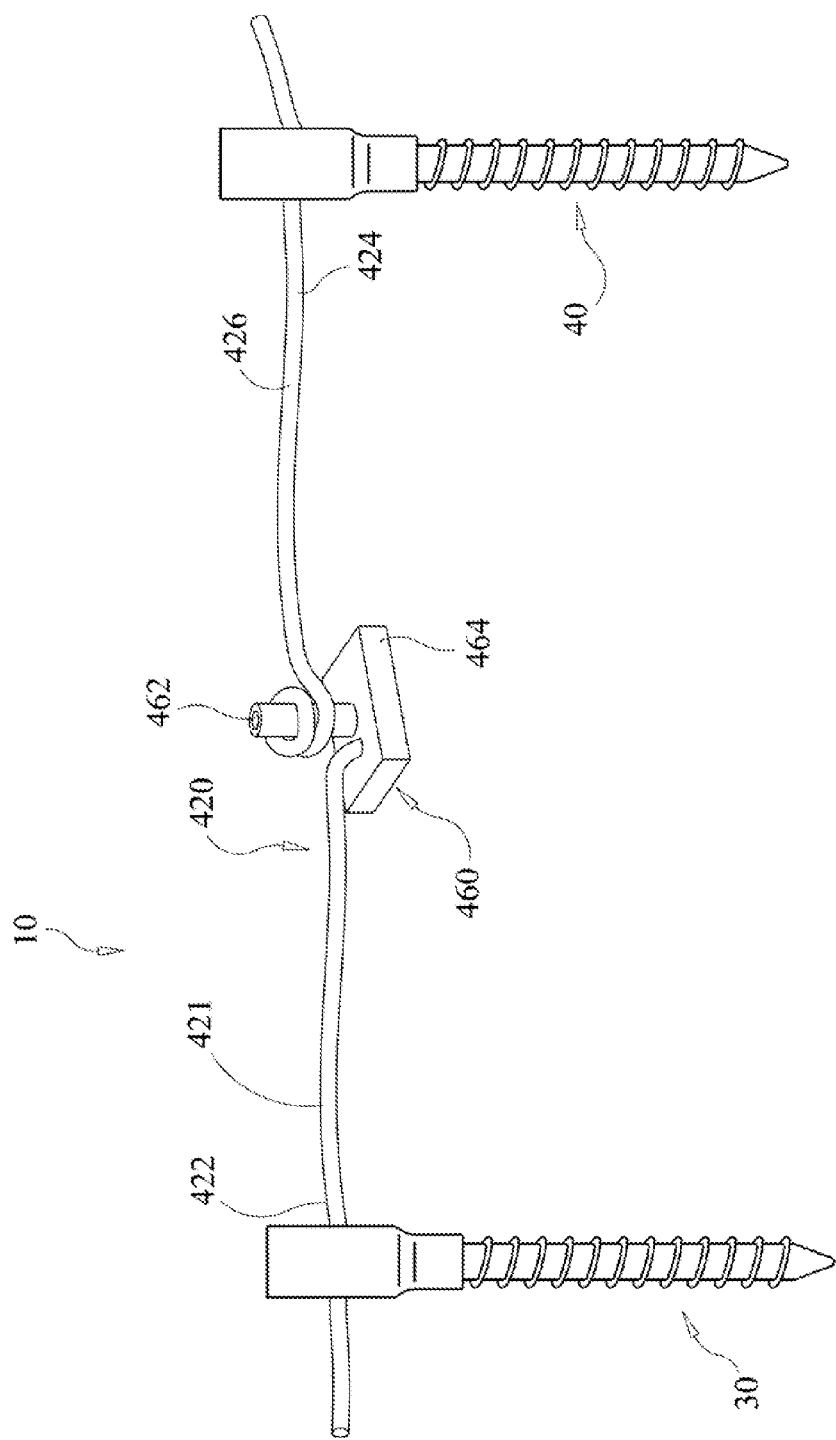
FIG. 10 is a perspective view of components of one embodiment of a surgical system in accordance with the principles of the present disclosure.

In one embodiment, as shown in FIG. 10, system 10, similar to the systems and methods described herein, includes a longitudinal element, such as, for example, at least one tether 420, similar to tether 20 described herein, extending between an end 422 and an end 424. Tether 420 includes a tether 421 and a tether 423. Tether 421, which includes end 422 of tether 420 has a fixed tension. System 10 includes a ratchet 460, similar to ratchet 260 described herein, disposed between bone screws 30, 40. Ratchet 460 includes a rotatable reel, such as, for example, a spool 462, similar to spool 62 described herein, rotatably engaged to a base 464. Tether 421 is connected to bone screw 30 and base 464 of ratchet 460 such that the tension of tether 421 is fixed between base 464 and bone screw 30. Tether 423, which includes end 424 of tether 420 has an adjustable tension and is connected to spool 462 and bone screw 40 such that rotation of spool 462 selectively adjusts the tension of tether 423.

Figure 11:
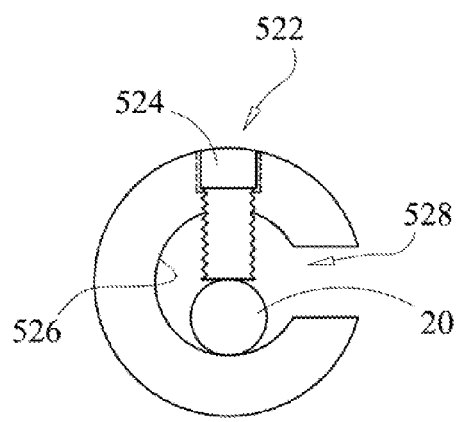
FIG. 11 is a side, cross-section view of components of one embodiment of a surgical system in accordance with the principles of the present disclosure.

In one embodiment, as shown in FIG. 11, system 10, similar to the systems and methods described herein, includes bone screws 30, 40. At least one of bone screws 30, 40 includes a C-shaped clamp 522 having a coupling member, such as, for example, a lock screw 524 engagable with tether 20. C-shaped clamp 522 has a diameter larger than a costo-vertebral space for fixed engagement with vertebrae to facilitate connection to the vertebrae and application of tension, as described herein. C-shaped clamp 522 has an inner surface 526 defining a cavity 528 configured for disposal of tether 20. With tether 20 disposed in cavity 528, lock screw 524 is axially translated into engagement with tether 20 to capture tether 20 between lock screw 524 and inner surface 526.

Figure 12:
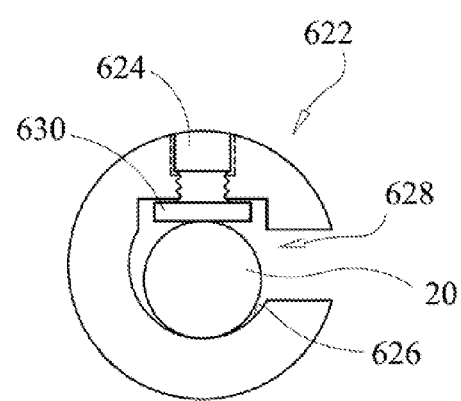
FIG. 12 is a side, cross-section view of components of one embodiment of a surgical system in accordance with the principles of the present disclosure.

In one embodiment, as shown in FIG. 12, system 10, similar to the systems and methods described herein, includes bone screws 30, 40. At least one of bone screws 30, 40 includes a C-shaped clamp 622, similar to C-shaped clamp 522 described herein, for fixed engagement with vertebrae to facilitate connection to the vertebrae and application of tension, as described herein. C-shaped clamp 622 includes a coupling member, such as, for example, a lock screw 624, similar to lock screw 524 described herein. C-shaped clamp 622 has an inner surface 626 defining a cavity 628 configured for disposal of tether 20. C-shaped clamp 622 includes a plate 630 disposed in cavity 628 between tether 20 and lock screw 624. With tether 20 disposed in cavity 628, lock screw 624 is axially translated to dispose plate 630 into engagement with tether 20 to capture tether 20 between plate 630 and inner surface 626.

Figure 13:
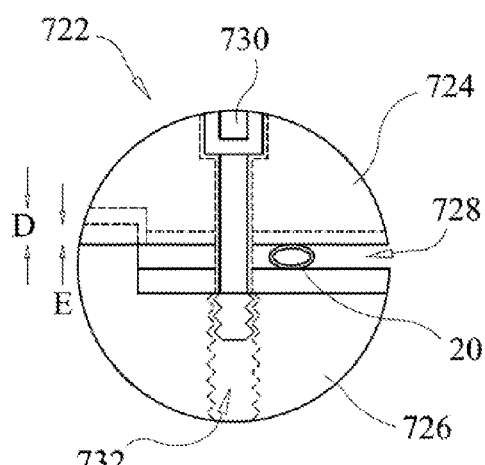
FIG. 13 is a side, cross-section view of components of one embodiment of a surgical system in accordance with the principles of the present disdosure.

In one embodiment, as shown in FIG. 13, system 10, similar to the systems and methods described herein, includes bone screws 30, 40. At least one of bone screws 30, 40 includes a clamp 722 for fixed engagement with vertebrae to facilitate connection to the vertebrae and application of tension, as described herein. Clamp 722 includes a portion 724 and a portion 726 movable relative to portion 724. Portions 724, 726 together define an expandable cavity 728 configured for disposal of tether 20. Cavity 728 includes a rectangular configuration. In some embodiments, cavity 728 is variously configured, such as, for example, those alternatives described herein. Clamp 722 includes a coupling member, such as, for example, a lock screw 730, similar to lock screw 524 described herein, disposed in a passageway 732 extending through portions 724, 726 substantially perpendicular to cavity 728. Lock screw 730 is configured to expand and/or contract cavity 728, in directions shown by arrows D and E in FIG. 13. With tether 20 disposed in cavity 728, lock screw 730 is axially translated in a first direction to move portions 724, 726 toward one another such that tether 20 is captured in cavity 728 between portions 724, 726. To release tether 20 from cavity 628, lock screw 730 is axially translated in a second direction, opposite the first direction to move portions 724, 726 apart from one another expanding cavity 728.

Figure 14:
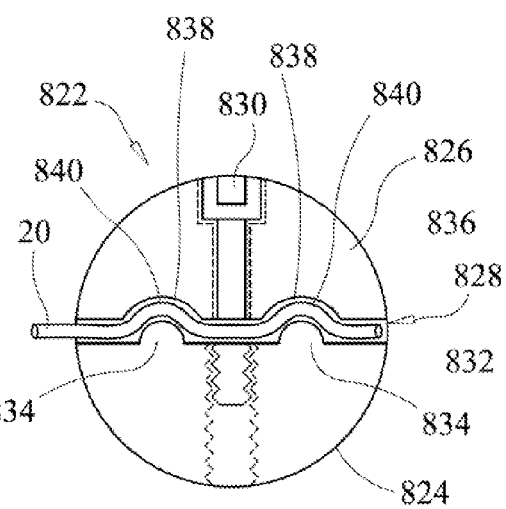
FIG. 14 is a side, cross-section view of components of one embodiment of a surgical system in accordance with the principles of the present disclosure.

In one embodiment, as shown in FIG. 14, system 10, similar to the systems and methods described herein, includes bone screws 30, 40. At least one of bone screws 30, 40 includes a clamp 822, similar to clamp 722 described herein, for fixed engagement with vertebrae to facilitate connection to the vertebrae and application of tension, as described herein. Clamp 822 includes a portion 824 and a portion 826 movable relative to portion 824. Portions 824, 826 together define an expandable cavity 828 configured for disposal of tether 20. Clamp 822 includes a coupling member, such as, for example, a lock screw 830, similar to lock screw 830 described herein, configured to expand and/or contract cavity 828. Portion 824 includes an inner surface 832 defining ribs 834 extending therefrom into cavity 828. Portion 826 includes an inner surface 836 defining notches 838 disposed in coaxial alignment with ribs 834. With tether 20 disposed in cavity 828, lock screw 830 is axially translated to move portions 824, 826 toward one another such that ribs 836 engage portions 840 of tether 20 to capture portions 840 of tether 20 in notches 838.

In some embodiments, the components of spinal correction system 10 and methods of use as described herein for tethering of deformities may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and methods of use as described herein may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   at least one tether extending between a first end connectable with a first fastener connected with spinal tissue and a second end connectable with a second fastener connected with spinal tissue, the at least one tether having a tension between the fasteners; and
   a ratchet engageable with the at least one tether to adjust the tension, the ratchet includes a rotatable reel configured for rotation in two directions to adjust the tension, the rotatable reel being axially movable between a first configuration in which the reel is rotatable relative to the ratchet and a second configuration in which rotation of the reel is resisted.

2. A spinal construct as recited in claim 1, wherein the at least one tether includes a first tether connected to the first fastener and the ratchet and a second tether connected to the second fastener and the ratchet.

3. A spinal construct as recited in claim 1, further comprising a third fastener including the ratchet and being configured for penetrating spinal tissue between the first fastener and the second fastener.

4. A spinal construct as recited in claim 3, wherein the at least one tether includes a first tether having an adjustable tension and being connected with the first fastener and the ratchet, and a second tether having a fixed tension and being connected with the second fastener and the third fastener.

5. A spinal construct as recited in claim 1, wherein the rotatable reel includes a male mating part engageable with the ratchet.

6. A spinal construct as recited in claim 1, further comprising a third fastener configured for penetrating spinal tissue and including the ratchet, the ratchet comprising a rotatable reel engagable with the tether to selectively adjust the tension.

7. A spinal construct as recited in claim 6, wherein the reel is lockable to prevent rotation thereof.

8. A spinal construct as recited in claim 7, wherein the reel is biased to a locked configuration.

9. A spinal construct as recited in claim 1, wherein the ratchet is configured for magnetic actuation to adjust the tension.

10. A spinal construct as recited in claim 1, wherein the ratchet is configured to dynamically adjust the tension.

11. A spinal construct as recited in claim 1, wherein at least one of the fasteners comprises a C-shaped clamp having a coupling member engagable with the tether.

12. A spinal construct as recited in claim 1, wherein at least one of the fasteners comprises a clamp having an inner surface defining ribs.

13. A spinal construct comprising:
   a fastener including a ratchet having a reel engageable with an intermediate portion of a tether having a tension between ends thereof,
   wherein the reel is rotatable in two directions relative to the ratchet to adjust the tension, and wherein the reel is axially movable between a first configuration such that the reel is rotatable relative to the ratchet and a second configuration such that the rotation of the reel is resisted.

14. A spinal construct as recited in claim 13, wherein the ratchet extends between a first end defining a first cavity configured for disposal of a first end of the reel in the second configuration and a second end defining a second cavity configured for disposal of a second end of the reel.

15. A spinal construct as recited in claim 14, wherein the ratchet includes a biasing member disposed in the second cavity between the second end of the ratchet and the second end of the reel to resiliently bias the reel to the second configuration.

16. A spinal construct as recited in claim 13, wherein the reel includes an inner surface defining a bore configured for disposal of the at least one tether.

17. A method of treating a spine disorder, the method comprising the steps of:
   providing at least one tether extending between a first end connected with a first fastener and a second end connected with a second fastener, the at least one tether having a tension between the fasteners;
   providing a ratchet for connection with an intermediate portion of the at least one tether;
   engaging the first fastener with a first costo-vertebral surface and engaging the second fastener with a second costo-vertebral surface; and
   engaging the ratchet and a reel to rotate the reel in two directions to selectively adjust the tension, wherein the step of engaging the ratchet comprises axially translating the reel between a first configuration such that the reel is rotatable relative to the ratchet and a second configuration such that rotation of the reel is resisted.

* * * * *